United States Patent
Komann

(10) Patent No.: US 10,195,348 B2
(45) Date of Patent: Feb. 5, 2019

(54) SYRINGE WITH FINGER FLANGE

(71) Applicant: Schott Schweiz AG, St. Gallen (CH)

(72) Inventor: Christian Komann, St. Gallen (CH)

(73) Assignee: SCHOTT SCHWEIZ AG, St. Gallen (CH)

( * ) Notice: Subject to any disclaimer, the term of this patent is extended or adjusted under 35 U.S.C. 154(b) by 0 days.

(21) Appl. No.: 14/938,138

(22) Filed: Nov. 11, 2015

(65) Prior Publication Data

US 2016/0129193 A1 May 12, 2016

(30) Foreign Application Priority Data

Nov. 11, 2014 (DE) .................. 10 2014 116 396

(51) Int. Cl.
*A61M 5/31* (2006.01)
*A61M 5/315* (2006.01)

(52) U.S. Cl.
CPC ...... *A61M 5/3137* (2013.01); *A61M 5/31511* (2013.01); *A61M 2005/3139* (2013.01); *A61M 2005/3143* (2013.01)

(58) Field of Classification Search
CPC .. A61M 2005/3139; A61M 2005/3142; A61M 5/3137; A61M 5/3135; A61M 2205/586
USPC ........................................................ 604/227
See application file for complete search history.

(56) References Cited

U.S. PATENT DOCUMENTS

| | | | |
|---|---|---|---|
| 4,711,637 A | 12/1987 | Leigh et al. | |
| 5,338,309 A | 8/1994 | Imbert | |
| 5,700,247 A * | 12/1997 | Grimard | A61M 5/315 604/220 |
| 5,997,514 A * | 12/1999 | Balestracci | A61M 5/3135 604/187 |
| 6,296,625 B1 * | 10/2001 | Vetter | A61M 5/3135 604/227 |
| 6,840,921 B1 * | 1/2005 | Haider | A61M 5/19 604/191 |
| 8,303,548 B2 * | 11/2012 | Ito | A61M 5/3135 604/164.08 |
| 2005/0148944 A1 * | 7/2005 | Hsieh | A61M 5/3243 604/198 |
| 2008/0188799 A1 | 8/2008 | Mueller-Beckhaus et al. | |
| 2013/0043282 A1 * | 2/2013 | Niklasson | A61M 5/31586 222/390 |
| 2015/0328408 A1 * | 11/2015 | Evans | A61M 5/3137 604/227 |

FOREIGN PATENT DOCUMENTS

| | | |
|---|---|---|
| DE | 102004017004 A1 | 10/2004 |
| DE | 102004036051 A1 | 2/2006 |
| DE | 102006005784 A1 | 8/2006 |

(Continued)

*Primary Examiner* — Nathan R Price
*Assistant Examiner* — John Doubrava
(74) *Attorney, Agent, or Firm* — Ohlandt, Greeley, Ruggiero & Perle, L.L.P.

(57) ABSTRACT

A syringe having a finger flange and a finger support is provided. The finger flange includes a radially projecting support surface for a finger and is joined to the syringe body of the syringe at its proximal end. In this case, the finger flange is further designed in one piece and includes at least two finger flange elements, which are movably joined with one another.

21 Claims, 4 Drawing Sheets

(56) References Cited

FOREIGN PATENT DOCUMENTS

| | | |
|---|---|---|
| DE | 4323124 B4 | 8/2013 |
| WO | 2011122351 A1 | 10/2011 |
| WO | 2011133097 A1 | 10/2011 |
| WO | 2013009387 A1 | 1/2013 |

\* cited by examiner

SYRINGE WITH FINGER FLANGE

CROSS REFERENCE TO RELATED APPLICATIONS

This application claims benefit under 35 U.S.C. § 119(a) of German Patent Application No. 10 2014 116 396.6 filed Nov. 11, 2014, the entire contents of which are incorporated herein by reference.

BACKGROUND OF THE INVENTION

1. Field of the Invention

The invention relates to a syringe having a finger flange and a finger support. Further, the invention relates to such a finger flange.

2. Description of Related Art

Syringes with an elongated cylindrical syringe body, in which a movable plunger is disposed in the direction of the longitudinal axis, are generally known. This type of syringe is usually produced from plastic or glass. At the distal end of the syringe body, there is generally a conical syringe piece which can be connected to a needle holder or a device for uptake of a needle. Further, the syringe body generally has a proximal open end, into which the plunger can be inserted.

The inner volume formed in the syringe body can be filled with a substance. By a stroke movement of the plunger, the substance can be expelled therefrom at the distal end of the syringe body through an outlet. In order to facilitate handling during the stroke movement, frequently a so-called finger flange is provided, this flange having a support for the finger.

In many cases, the finger flange is formed in one piece together with the syringe body. This is a relatively simple thing to do, for example, in the case of a syringe body made of plastic. In contrast, if syringe bodies made of glass are used, then strict structural limits are placed on the design of a suitable finger flange from the glass body. This is even more the case when the syringe body is fabricated, for example, from a piece of glass tubing. In order to ensure a sufficient strength of the finger flange, greater reshaping of the glass tubing or even a fabrication with over-dimensioning is necessary.

In order to avoid this, different finger flanges for subsequent mounting on a syringe have been developed.

Thus, for example, a syringe having a finger flange that can be axially pushed onto the syringe body can be derived from Patent DE 43 23 124 B4. The finger flange therein is formed in such a way that it has an opening that is dimensioned so that when it is pushed on, it is pressed on and subsequently locked in a region provided for this. In the case of this method, the great effort that is placed on the accuracy of the outer geometry of the syringe body can be viewed as unfavorable, so that pushing on the finger flange is only generally made possible. The opening of the finger flange is widened by the pushing on.

Another form for a finger flange that can be subsequently mounted on a syringe is disclosed in DE 10 2004 036 051 A1. A finger flange is proposed, which can be mounted on the distal end of the syringe body via laterally pushing it on in a region of the syringe body provided for this. The finger flange proposed therein is in fact easy to mount. Of course, this prior art flange can also be easily disassembled and it is not secure against an unintentional loosening. A twisting relative to the syringe body is also possible, so that handling the finger flange can become difficult.

Further, document DE 10 2006 005 784 discloses a syringe with a cylindrical syringe body, for which a multi-part component that is formed as a finger flange is provided. The finger flange can be joined to the proximal end of the syringe body and is designed so that it cannot be removed without adversely affecting the syringe body. A disadvantage of this embodiment is the multi-part construction, which leads to an increased expenditure with respect to storage and logistics as well as a complicated mounting.

SUMMARY

The object of the present invention, which results therefrom, is to be seen in the provision of a syringe with a finger flange, wherein the finger flange can be mounted subsequently on the syringe. Further, a corresponding finger flange shall be provided.

In this case, the finger flange shall be able to be joined solidly with the syringe without it being able to be disassembled again. Further, it shall also be secure against twisting on the syringe when it is in the mounted state. A mounting of the finger flange shall also be possible in the case of slight deviations in shape and position of the syringe, in particular, in the region of the proximal end.

The finger flange shall be able to be fabricated in large numbers of pieces in a cost-favorable manner. Therefore, the finger flange shall be formed in one piece as much as possible, preferably from a single material, and/or shall be able to be manufactured by means of a simple fabrication process aligned to large numbers of pieces.

This object is achieved in a surprisingly simple way by a syringe as well as a finger flange as disclosed herein.

Accordingly, the invention relates to a syringe, comprising a cylindrical syringe body having a distal end and a proximal end, as well as a finger flange having at least one support surface for a finger, wherein the syringe body comprises a cylindrical chamber for uptake of a liquid substance; the proximal end of the syringe body has an opening through which a plunger can be guided; the proximal end of the syringe body further comprises at least one projection that protrudes radially outward, projecting over the circumferential surface of the syringe body; the finger flange is designed in one piece; the finger flange comprises at least one first and one second finger flange element, which are movably connected to one another and can be moved from an open position to a closed position; in closed position, the finger flange is connected in a friction-fit at least partially to at least one projection and surrounds the projection at least partially in such a way that, in closed position, an axial displacement of the finger flange relative to the syringe body is prevented, and wherein the finger flange has a recess for guiding the plunger through it.

The distal end of the syringe body is thus designed for joining to a needle or a needle uptake device. The syringe body further comprises a chamber for the uptake of a liquid substance or a fluid. The syringe can be either unfilled, or it can also be already filled with the substance. In the filled state, a stopper is generally provided, which seals the chamber in a fluid-tight manner in order to avoid an undesired leakage of the substance. The distal end of the syringe can have an outlet for expelling the substance.

The proximal end of the syringe body further has an opening through which a plunger can be introduced into the chamber.

In the region of the proximal end, the syringe body can be formed with at least one projection protruding outward, which thus projects over the outer cylindrical surface of the syringe body. This can be a protruding ring-shaped or annular circumferential projection, for example, or also an annular circumferential bead. The syringe body can also comprise a groove on its proximal end.

In the sense of the invention, the finger flange can be joined with the proximal end of the syringe body in a friction-fit and/or a form-fit. Preferably, in the closed position, it is thus secured simultaneously against an undesired loosening. In this case, the finger flange can comprise at least one first and one second finger flange element, these elements being movably disposed relative to one another and can be moved from an open position into a closed position. Preferably, the open position serves for a simple mounting of the finger flange on the syringe body, whereby then the form-fitting connection can be created by a closing movement.

Due to the friction-fitting and/or form-fitting connection, which is created between the finger flange and the syringe body in closed position of the finger flange, an axial movement of the finger flange relative to the syringe body, thus a relative movement parallel to the center line of the syringe body, is prevented. In this case, at least a part of the finger flange and/or of the finger flange element can surround the syringe body at its proximal end, at least partially, or also encircle it completely.

In addition, the finger flange has at least one, preferably continuous, recess, which is disposed in mounted position advantageously congruent to the opening of the syringe body, so that the guiding of the plunger is made possible by a finger flange mounted on the syringe body. This recess may also be a continuous opening.

A plunger can be introduced into the chamber through the opening in the proximal end of the syringe body and through the continuous recess or opening in the finger flange. This plunger can be used, for example, in the case of a syringe filled with a substance, for the purpose of moving the stopper. For this purpose, for example, the plunger can be screwed into the stopper into a thread provided therefor, and thus can be solidly joined to the latter.

In another embodiment, the syringe is not filled. The plunger can then be designed with an end piece sealing the chamber in a fluid-tight manner, so that a substance can be drawn into the chamber of the syringe body through the opening in the distal end by means of an axial stroke movement in the direction of the proximal end, and then can be expelled again later by a reversed stroke movement of the plunger in the direction of the distal end. Also, however, a plunger with a stopper attached thereon can be introduced into the chamber.

The mounting sequence of finger flange and plunger can be different. Thus, the finger flange can be mounted first and then the plunger; however, a reversed mounting sequence is also possible.

In an advantageous way, the recess of the finger flange is designed as elastic or partially elastic in this case, so that the plunger can in fact be introduced, but then can no longer be subsequently withdrawn. This can be made possible, for example, by means of an elastic recess expanding only in one direction when the plunger is pushed in, this recess preventing a snapping back and pulling out after the plunger has been pushed in. This security against the pulling out of the plunger is also called a "backstop" function.

This configuration is particularly favorable in the case of a mounting sequence in which the plunger is mounted after the finger flange. It can be assured in a simple way by the backstop function of the finger flange that the plunger will not be accidentally removed again and the syringe rendered unusable.

In another embodiment, the recess of the finger flange is designed in such a way that the stopper is prevented from being pulled out. This backstop function accordingly serves as a prevention measure against the pulling out of the stopper. In this embodiment, the plunger can be designed smaller or thinner.

Further, the finger flange comprises at least one support surface for a finger, this surface projecting radially outward for the support of a finger. Preferably, at least two opposite-lying finger supports are provided, so that a particularly secure and stable support is possible and thus a secure handling can be created.

In the sense of the invention, a finger flange comprises at least one first and one second finger flange element these elements being joined together in movable manner, preferably movable by rotation.

According to the invention, the finger flange is designed in one piece. It is particularly to be understood by this that the finger flange can be provided as a single component for mounting on the syringe body. A cost-effective fabrication in large numbers of pieces is possible thereby. Also, costs for transport and logistics can be minimized. The finger flange elements of the finger flange are joined together in this case in such a way that a separation is possible only by surmounting a certain resistance, in order to exclude an undesired or unintentional separation. It is particularly preferred that the finger flange elements are not separable from one another in a nondestructive manner. It can be assured in this way that an already mounted finger flange cannot be disassembled again and subsequently mounted repeatedly.

These at least two finger flange elements of the one-piece finger flange can be joined together in form-fitting manner in this case by means of a joint or hinge, preferably by means of a rotating joint or hinge. The finger flange elements can be joined together in movable manner in this way, preferably movable by rotation.

In a particularly preferred embodiment, the finger flange elements of the one-piece finger flange can also be joined together cohesively, movability also being able to be produced by means of a joint or hinge.

Preferably, the finger flange elements are joined together in a manner movable by rotation, so that a rotational movement of the at least one finger flange element relative to the at least one other finger flange element is made possible.

In this case, the axis of rotation of the finger flange elements can run along or parallel to a common straight edge. This axis of rotation—in the mounted state—can be either parallel or perpendicular to the center line of the syringe body. By a rotational movement of the finger flange elements relative to one another, the finger flange can be brought from an open position into a closed position, in particular after mounting on the syringe body. The finger flange elements can form at least one common contact surface thereby.

In this way, the finger flange, for example, in the open state, for attaching to the syringe body, at first can be joined with the first finger flange element by plugging it on, pushing it on or clamping it with the syringe body, and then can be brought into a closed position by a simple rotational movement of the second finger flange element of the finger flange, so that a form-fitting connection can be produced to at least the region of the proximal end of the syringe body comprising the projection.

A joint or hinge can be provided for producing a movable, preferably rotatable, connection between the finger flange elements.

In one embodiment of the finger flange with cohesively joined finger flange elements, the joint or hinge can be a bendable fold or a thin-walled connection, which makes possible a rotational movement. More particularly preferred, it involves a foil joint or film joint or a film hinge. In this way, the joint or hinge can be produced from the same material as the finger flange, so that a particularly cost-effective production is made possible for large numbers of pieces in the injection molding process.

In the sense of the invention, however, the one-piece finger flange can also be formed from at least two finger flange elements that are joined together in such a way that they can be separated only by surmounting a certain resistance. In this case, the finger flange elements can be joined together in form-fitting manner by means of a joint or hinge.

The finger flange elements can be produced from a first material, which is rigid or has no elasticity or has only a small amount of elasticity, and thereafter, a second material that provides the elasticity necessary for the rotational movement can be provided. Such a finger flange can be produced in a very cost-effective manner and in large numbers of pieces, for example, by a multi-component injection molding.

A manufacture of the finger flange according to the in-mold process, in which two or more components or finger flange elements are produced in common, is also viewed in the sense of the invention. In the case of a finger flange produced in such a way, two finger flange elements joined together in form-fitting manner are thus also considered as one-piece in the sense of the invention. A cost-effective fabrication with very large numbers of pieces is also possible with this method.

In this way, the finger flange can also comprise a material with a greater elasticity in the contact region with the syringe body or in the region with the recess than in the other regions. Thus, the finger flange elements can be produced of PP, for example, and can comprise an elastomer in the region of the recess and/or in the region of the rotatable connection or in the region of the joint or hinge. In this way, geometric deviations of the syringe body can be compensated.

In this way, the finger flange can be produced in one piece, whereby, in the mounted state, a very solid and stable connection to the syringe body can be produced. Simultaneously, however, the necessary movability of the finger flange elements relative to one another also can be assured.

Advantageously, the finger flange, at least in the region of the joint or hinge, is produced from a partially elastic or semi-elastic material, in order to assure movability. The known familiar materials can be used for this purpose, comprising polypropylene (PP), polyethylene (PE), polyoxymethylene (POM), polybutylene terephthalate (PBT), polyamide (PA), polyethersulfone (PES), thermoplastic elastomer (TPE), but also glass-fiber-reinforced plastics, for example. In this way, the finger flange can be manufactured in a particularly simple way by means of common methods, such as injection molding.

In a preferred embodiment, at least the first finger flange element is formed with a recess in this case, preferably with a U-shaped recess, in order to be connected in form-fitting manner, at least partially, with the region of the proximal end of the syringe body comprising the projection. Advantageously, therefore, the contact region of the finger flange element, in particular in the region of the recess, is formed with an inner contour that is at least partially precisely diametrically opposite the outer contour of the proximal end of the syringe body.

It is preferably formed precisely diametrically opposite the projection or the groove. In other words, the contact region of at least one finger flange element is adapted to the outer contour of the proximal end of the syringe body, in particular to the projection, in such a way that, in closed position, the finger flange makes possible a friction-fitting and/or form-fitting connection between finger flange and syringe body.

In this case, the at least one finger flange element can comprise the peripheral surface of the syringe body in a prespecified region. It is then advantageous, e.g., if the projection annularly surrounds the syringe body, at least partially. In one favorable embodiment, which is particularly user-friendly to mount, at least the first finger flange element encircles the peripheral surface of the syringe body in a region that has an included angle of at most 180°, so that the finger flange element can be pushed onto the peripheral surface in a particularly simple manner. Therefore, an embodiment in which the included angle is less than 180° and preferably less than 175° can also be very favorable, since, in this way, the finger flange element can be joined very simply in form-fitting manner to the proximal end of the syringe body.

In a particularly favorable embodiment, a second finger flange element is provided, which is formed largely complementary to the first finger flange. After mounting the first finger flange element, the finger flange can then be closed in a particularly simple manner by means of a rotational movement of the finger flange, and the peripheral surface of the syringe body can be enclosed almost completely in form-fitting manner by the finger flange. The axis of rotation of the finger flange element can be disposed parallel to the center axis of the syringe body in this embodiment.

The finger flange according to the invention can comprise additional finger flange elements that can be joined likewise in a movable, preferably rotatable manner, with at least one other finger flange element. Preferably, these other finger flange elements are joined together cohesively.

In another favorable embodiment, the finger flange can comprise three finger flange elements, for example, which are joined together in a rotatable manner relative to one another by means of two film hinges and which each have a recess with an inner contour that is formed precisely diametrically opposite the peripheral surface of the syringe body. In this case, in a preferred embodiment, each finger flange element can comprise the peripheral surface of the syringe body in a region that amounts to an included angle of approximately 60°, so that all finger flange elements can be placed in a particularly simple manner onto the peripheral surface of the syringe body, and the individual finger flange elements can be brought into a closed position by corresponding rotational movements, so that, in the closed state, the finger flange encircles the syringe body completely in form-fitting manner.

In the sense of the invention, it is further provided that the finger flange elements in the closed position are joined together and/or are joined to the syringe body in such a way that an undesired loosening is reliably prevented. A locking or a latching of the finger flange elements can be provided for this purpose. In other words, the finger flange elements can be solidly locked together, for example, in the closed position, in order to prevent an opening.

In the case of two finger flange elements, for example, locking can occur automatically after mounting via a rotational movement about the common axis of rotation. For this purpose, for example, a locking element can be provided on a first finger flange element, this locking element engaging in a complementary uptake element of a second finger flange element and in this way creating a form-fitting, permanent connection, which at the same time prevents an undesired loosening.

It is likewise also possible that the finger flange elements in closed position are cohesively joined together and/or are joined with the syringe body. For example, the finger flange elements can be glued together and/or glued to the syringe body for this purpose. An undesired removal of the mounted finger flange can thus be prevented. A cohesive connection also offers the advantage that at the same time, the finger flange is also secured against a twisting about the center axis of the syringe body.

In an enhancement of the invention, the recess of the finger flange can be formed elastically in the contact region with the projection, in order to create a compensation of tolerances with respect to the syringe body. Preferably, in this case, the recess has a certain dimension in the contact region, so that, in the mounted state, in addition to the form fitting, a friction closure or a clamping is effected, which counteracts a rotational movement of the finger flange about the syringe body. Therefore, a rotational movement of the mounted finger flange about the center axis of the syringe body can be counteracted and a twisting of the finger flange can be prevented.

The finger flange can have, at least a partially, a groove for this purpose, for example, which is formed for the purpose of taking up and/or encircling the projection of the syringe body. This groove can be designed to be elastic. A clamping of the projection in the mounted state can be achieved by the dimension of the groove.

Deviations in form and position of the syringe body and/or of the projection can also be advantageously compensated by an elastic design of the finger flange in the contact region with the syringe body. This is particularly favorable if the syringe body is manufactured of glass and the projection is produced by a hot-forming process. Certain geometric deviations of the syringe body often cannot be completely excluded thereby.

In an additionally preferred embodiment, a finger flange element, in particular for facilitating mounting on the front side of the proximal end of the syringe body, can comprise a centering aid. This aid can be formed, for example, precisely diametrically opposite the inner contour of the opening on the proximal end of the syringe body.

The invention further comprises a one-piece finger flange having at least one first and one second finger flange element for mounting on a proximal end of a syringe body. In this case, the individual finger flange elements are joined together in a movable manner, preferably rotatable. At least one joint or hinge, preferably a foil joint or film joint can be provided for this purpose. A finger flange can also comprise more than two finger flange elements.

A finger flange according to the invention can subsequently be mounted on a syringe body. In this case, its inner contour is preferably adapted to the peripheral surface of the syringe body at its proximal end, in particular to the outer contour of the projection. In this way, it is possible to retrofit syringes with a finger flange according to the invention or to equip them with a finger support surface.

In the sense of the invention, on the one hand, a finger flange is very simple to mount on the syringe, so that a flexibility that is as great as possible is afforded relative to the mounting. In addition, however, it is also easy to manufacture, for example, as a one-piece injection molding. The requirements relative to transport, storage and logistics are also relatively few in this case.

In the mounted state, the finger flange is further characterized by protection against disassembling. It can also be formed secure against twisting by the additional groove, so that a solid seating on the syringe is assured. In addition, it can also comprise a compensation of tolerances relative to deviations in shape or position of the syringe body.

DETAILED DESCRIPTION

In the following detailed description of preferred embodiments, the same parts in or on these embodiments are essentially designated by the same reference numbers for the sake of clarity.

It is obvious to the person skilled in the art that the invention is not limited only to the exemplary embodiments described above on the basis of the figures, but rather can be varied in many ways within the scope of the subject of the patent claims. In particular, the features of individual embodiment examples may also be combined with one another. The dimensions and proportions in the figures may deviate from the actual sizes for reasons of better illustration.

Figure 1:
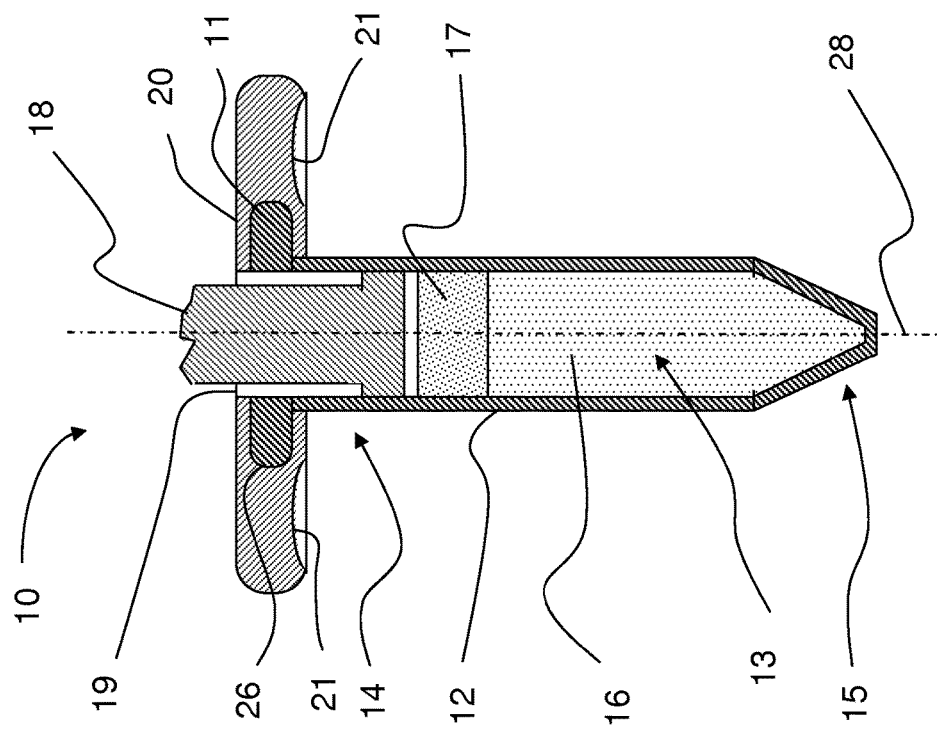
FIG. 1 shows schematically an exemplary syringe having a finger flange in the mounted state, in section.

FIG. 1 shows schematically in section an exemplary syringe 10 having a finger flange 20 in mounted state, thus in a closed position. The syringe 10 comprises a cylindrical chamber 13 for uptake of a liquid substance. It can be unfilled, but it can also be manufactured already filled with a liquid. In the example, the syringe 10 is filled with a liquid 16.

The syringe 10 further comprises a distal end 15. In this region, the syringe can be connected to a needle or a needle uptake device (not shown) in order to expel the liquid 16 present in the chamber 13. The distal tip of the syringe 10 can have an outlet for this purpose. Also, an outlet through which the liquid 16 can be expelled can also be created by the connection of the syringe 10 with a needle.

In addition, the syringe 10 comprises a proximal end 14, which is formed with a circumferential projection on the front side, in the example with an annular circumferential projection 11 protruding over the cylindrical surface of the syringe body. The projection 11 may be formed as encircling or, for example, may be disposed only on one side of the syringe body. On the front side, the syringe 10 has an inner opening 19, through which a plunger 18 can be introduced into the chamber 13. In the filled state, the syringe 10 is equipped with a stopper 17, which seals the chamber 13 in a fluid-tight manner against an undesired leakage of the substance 16. The plunger 18 can be introduced into the chamber 13 and connected to the stopper 17, for example, by screwing it into a threaded borehole prefabricated in the stopper. In this way, the stopper 17 can be moved axially in the chamber 13 by means of the plunger 18, and the liquid 16 can be expelled via a stroke movement in the direction of the distal end. In the case of an unfilled syringe 10, however, the plunger can also be designed in such a way that it seals the inner wall of the chamber 13 in a fluid-tight manner. By means of a stroke movement in the direction of the proximal end 14, a liquid can then be drawn into the chamber 13 through the distal end and can be expelled again via a reversed stroke movement.

In order to facilitate the handling of such a syringe 10, a finger support is helpful, the use of which is assumed to be sufficiently known, so that a detailed description will be omitted here.

For connection to a syringe 10, a finger flange 20 that has at least one finger support 21 is proposed according to the invention. In this case, in closed position, the finger flange 20 is connected in form-fitting manner to the projection 11 of the syringe body 12, whereby at least one common contact surface is formed between the finger flange 20 and the projection 11. In this way, an axial displacement of the finger flange 20 relative to the syringe body 12 can be prevented.

In the example illustrated, the finger flange 20 comprises two finger support surfaces 21, which are disposed lying opposite one another and project radially outward beyond the syringe body 12. A particularly simple and reliable handling of the syringe 10 can be assured therewith.

The inner contour of the finger flange 20 is thus designed in such a way that it is formed precisely diametrically opposite the outer contour of the syringe body 12, and particularly of the projection 11. In other words, the inner contour of the finger flange 20 is adapted to the outer contour of the circumferential annular projection 11 of the syringe body in such a way that, in closed position, a form-fitting connection can be created. In the mounted state, the finger flange at least partially surrounds the circumferential annular projection. In this case, the finger flange 20 comprises a recess, a through-opening in the example, for passage of the plunger, the inner diameter of this passage being tailored to the opening 19 of the syringe 10.

In the sense of the invention, the finger flange 20 is formed in one piece, in order to assure a particularly simple manufacturability. In this case, it can completely comprise an elastic material or can comprise an elastic material only in specific regions. The elastic material can be a thermoplastic material, which is characterized by a light weight and a simple malleability. For the film hinge and/or the contact region between finger flange 20 and syringe body 12, known familiar materials can be used, comprising polypropylene (PP), polyethylene (PE), polyoxymethylene (POM), polybutylene terephthalate (PBT), polyamide (PA), polyethersulfone (PES), thermoplastic elastomer (TPE), but also glass-fiber-reinforced plastics, for example. Therefore, particularly cost-effective injection molding methods are also possible for the manufacture of the finger flange 20.

In closed position, the finger flange 20 surrounds the at least one projection 11, so that a form-fitting connection can be created. This form-fitting connection prevents an axial movement of the finger flange 20 along the center line 28 of the syringe body 12, so that it is possible to create a very stable and reliable finger support.

In addition, the finger flange 20 can also be connected cohesively to this support, e.g., by means of gluing, in the region of the contact surface with the syringe body 12, in order to create an even greater stability of the connection, and on top of this, to exclude an undesired loosening of the finger flange. Also, a safeguarding against a twisting of the finger flange relative to the syringe body can be realized thereby.

In the region of the projection 11, at least one finger flange element can have, in addition, at least partially, a groove 26, which is at least partially formed precisely diametrically opposite the projection 11 to be taken up, and runs along the recess. This recess can be fabricated with a slightly smaller size opposite the projection, so that the projection 11 is additionally clamped during the mounting. In this way, a safeguarding against a twisting of the finger flange 20 about the center line 28 can be assured in a very simple way.

Figure 2:
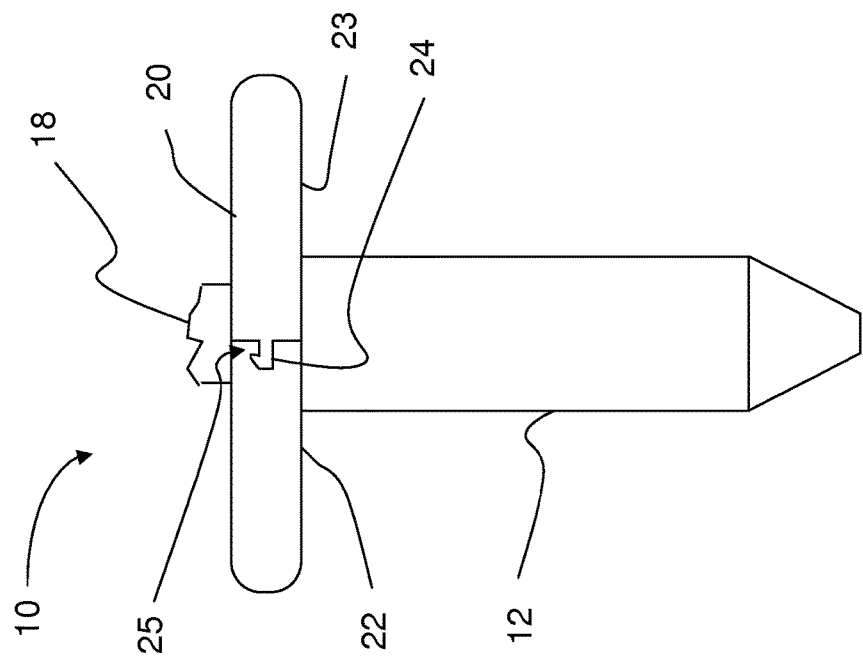
FIG. 2 shows schematically an exemplary syringe having a finger flange in the mounted state, in a lateral view.

FIG. 2 shows schematically an exemplary syringe 10 having a finger flange 20 in the mounted state, in a lateral view. The illustrated finger flange 20 comprises two finger flange elements 22, 23 that are formed substantially complementary to one another. Both finger flange elements 22, 23 have a recess with an inner contour that is precisely diametrically opposite the outer contour of the projection 11 of the syringe 10. In the mounted state, both finger flange elements 22, 23 completely surround the peripheral surface of the syringe body 12 at its proximal end 14.

The recesses are substantially formed in U-shape in the axial direction, in order to be able to optimally surround the circumferential projection 11. In this case, the recesses are disposed particularly advantageously in such a way that, in the mounted state, they form a through-opening, which matches the opening 19 of the syringe body 12 and thus the passage of the plunger 18 is made possible.

The finger flange 20 further comprises a joint or hinge for the rotatable connection of the two finger flange elements 22, 23, this joint being disposed on the back side and thus not visible in the figure, as well as opposite-lying locking elements for latching or locking the two finger flange elements in closed position. In the closed position, a locking element 24 of the first finger flange element 23 can engage in an uptake element 25 which is formed precisely diametrically opposite in the other second finger flange element 22, in order to be able to lock the two finger flange elements together so that they cannot loosen in the mounted state.

The locking or latching element 24 is only shown schematically and by way of example. It is particularly favorably formed in such a way that a latching is made possible, preferably during the rotational movement for closing the finger flange elements, and wherein simultaneously a re-opening is counteracted by the configuration of the latching elements. Therefore, an undesired re-opening and a loosening of the finger flange 20 from the syringe 10 will be prevented.

Therefore, an indissoluble connection of the two finger flange elements 22, 23 can result thereby. In this case, a first finger flange element 23 can be formed, for example, with a resilient elastic barb, which can engage in a precisely diametrically opposite uptake 25 of the second finger flange element 22.

The resilient elastic barb as well as the diametrically opposite uptake in this case can be formed in such a way that a re-opening is not possible without damaging the connection elements. The finger flange 20 can be connected to the syringe 10 in form-fitting manner and indissolubly in this way. An accidental removal of the finger flange 20 from the syringe body 12 can be counteracted in this way.

The finger flange is designed in one piece. In this case, it can comprise two or more finger flange elements, which are disposed in a movable, preferably rotatable manner, to one another, and are cohesively solidly joined with one another.

Figure 3:
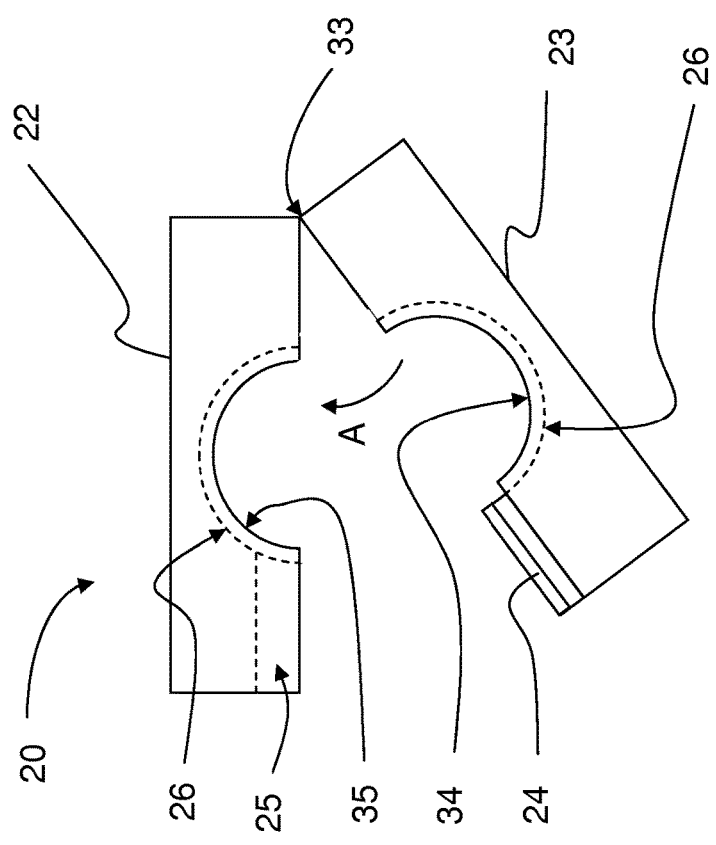
FIG. 3 shows schematically an embodiment of a finger flange in a top view.

FIG. 3 shows schematically an exemplary embodiment of a finger flange 20 in a top view. The figure shows a finger flange 20 in a form ready for mounting, thus before mounting on the syringe body 12. The two finger flange elements 22, 23 are thus shown in an open position. Depending on the manufacture, the open position may differ, of course, from the form illustrated.

The two finger flange elements 22, 23 are formed largely complementary to one another. Each of the two finger flange elements are cohesively and rotatably joined together along a common straight edge via a joint or hinge 33. The joint 33 can comprise a film hinge, a foil joint, or a film joint, which permits a rotational movement of the finger flange elements 22, 23 relative to one another, and defines an axis of rotation that runs along the common edge in the illustrated example.

In the illustrated example, the axis of rotation of the finger flange 20 lies parallel to the center line 28 of the syringe body 12, when the finger flange 20 is fully mounted on the syringe 10. The position of the axis of rotation relative to the center line 28 of the syringe body determines the type and manner of how the finger flange can be mounted on the syringe body and then closed. In other embodiments, the axis of rotation can also be disposed perpendicular to the center axis 28 of the syringe body 12.

The finger flange 20 is formed with a central passage opening, which results due to the shape of two equally large recesses 34, 35 in the two finger flange elements 22, 23. In this case, the recesses 34, 35 are of approximately U-shaped form and are adapted to the outer surface of the syringe body. In the mounted state, at least one section of the syringe body can be surrounded by the finger flange thereby, in such a way that the syringe body 12 is surrounded in a peripheral region, which corresponds to the one included angle of more than 180°. In the present example, the annular projection 11 of the syringe body 12 can be almost completely surrounded by the finger flange, which is formed with a groove 26 for this purpose, thus corresponding to an angle range equal to or nearly 360°. In this case, an individual finger flange element 22, 23 surrounds the annular projection only partially each time, presently in a peripheral region that corresponds to an included angle of approximately 180°.

Of course, other included angles are also possible. In the case of a finger flange 20, for example, with three finger flange elements complementary to one another, each individual finger flange element can include the syringe body 12, for example, in a peripheral region that corresponds to an included angle of 120°. In the closed state, due to the three individual finger flange elements, the finger flange then includes the annular projection at approximately 360°, so that a particularly stable, form-fitting connection can be created.

In this way, a particularly simple mounting of the finger flange 20 on the syringe body 12 is possible, since no additional force components are necessary for overcoming adhesive friction due to axial displacement or to the pressing on of the finger flange element.

The recess 34, 35, which is U-shaped in the axial direction, makes it possible to at least partially enclose a peripheral segment of the syringe body 12.

In this case, in an enhancement of the invention, at least one recess can be formed in a particularly favorable way with a groove 26 disposed centrally, running inwardly, this groove being formed with a slightly smaller dimension precisely diametrically opposite the outer contour of the projection 11 in such a way that, in addition to the form-fitting, the projection is also clamped. It is of advantage in this case, if the material of the finger flange element 22, 23, has an elasticity, at least in the contact region with the projection 11, so that slight deviations in the shape and position of the projection 11, and also in its outer contour or in the outer diameter of the syringe body 12 can be compensated.

The recess 34, 35 of the finger flange 20 is advantageously disposed in such a way that, in the mounted state, it is congruent with the opening 19 of the syringe body 12 and in this way creates a passage opening. In this way, the plunger 18 can be conducted through the passage opening of the finger flange 20 into the chamber 16 of the syringe body 12 and can be moved axially.

In a favorable embodiment, the locking element 24 as well as the uptake element 25 can be disposed on a side facing away from the common straight edge or opposite-lying side. In the illustrated example, an elastic spring element 24 of the finger flange element 23 for latching in the correspondingly formed recess 25 of the finger flange element 22 is arranged on the surfaces of the two finger flange elements 22, 23 that abut in the mounted state.

The finger flange 20 can be mounted on the syringe body 12, for example, in such a way that at first a first finger flange element 22 is pushed on or plugged onto the syringe body 12 and then can be closed by a rotational movement in direction A of the finger flange. A form-fit that is very stable can be created between finger flange 20 and projection 11 thereby.

Figures 4, 5:
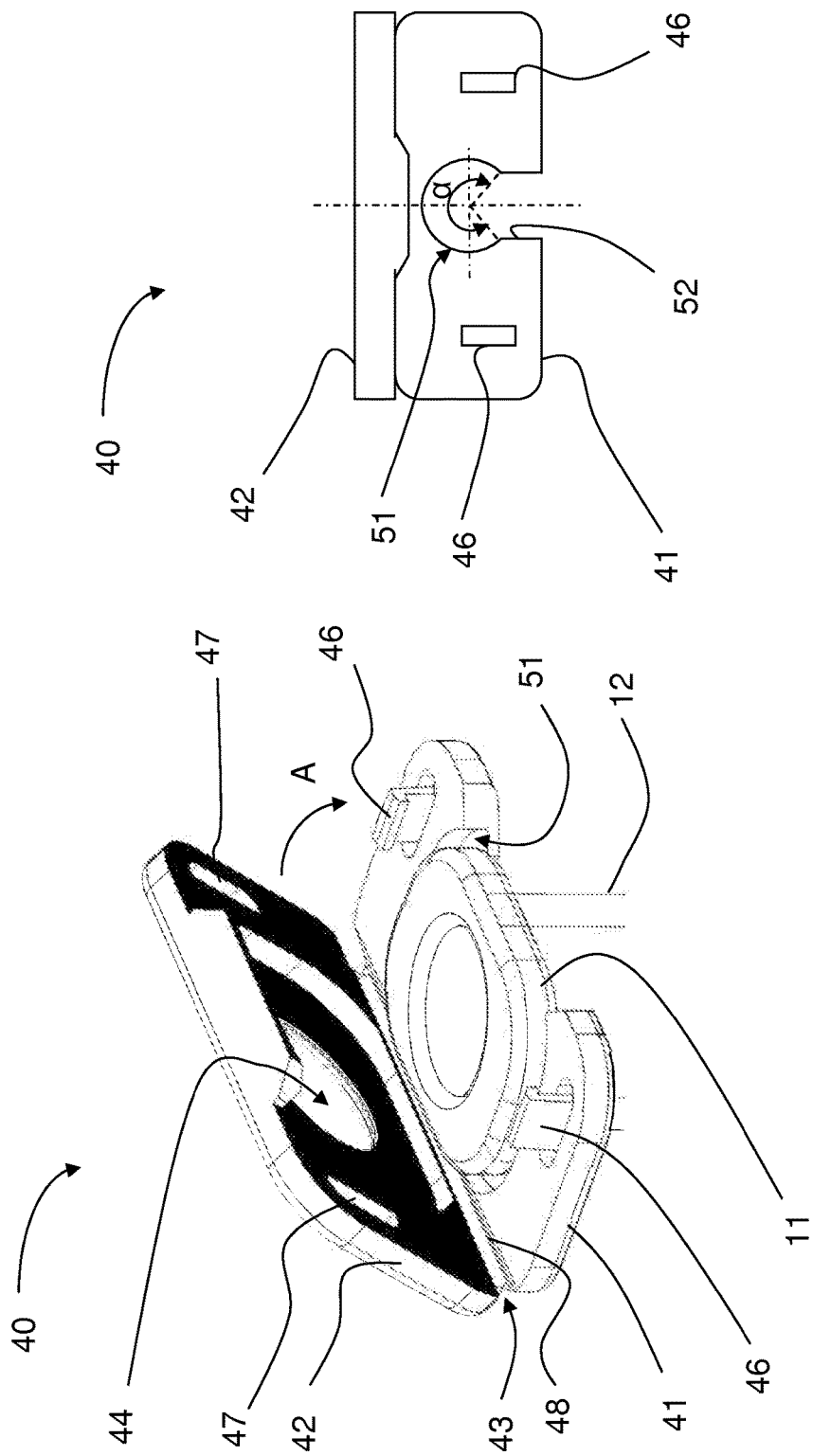
FIG. 4 shows schematically another embodiment of a finger flange, in a perspective oblique view.
FIG. 5 shows schematically another embodiment of a finger flange, in a top view.

Another preferred embodiment of a finger flange according to the invention is schematically shown in FIG. 4 in a perspective oblique view.

The illustrated finger flange 40 comprises two finger flange elements 41, 42, which abut one another along a common straight edge 48 and are cohesively and movably joined to one another. A joint, in the example a film hinge 43, is disposed along the common straight edge 48, so that both finger flange elements 41, 42 can be rotated about the axis of rotation formed by the hinge, from an open position into a closed position. In the illustrated example, this axis of rotation lies perpendicular to the center line 28 of the syringe body 12, when the finger flange 40 is mounted on the syringe 10.

In this embodiment, there is a contact surface between finger flange 40 and syringe body 12, which comprises both a part of the cylindrical surface, particularly in the region of the projection, as well as at least one part of the front side of the syringe body. At least one finger flange element 42 is thus formed precisely diametrically opposite the front side of the syringe body.

A first finger flange element 41 is formed in such a way that it has a recess 51, which makes possible a radial displacement onto the proximal end of the syringe body 12. In this case, a contact surface is formed between the projection 11 of the syringe body and the finger flange element 41, this contact surface comprising in the axial direction approximately half the portion of projection 11 pointing in the direction of the distal end of the syringe body. The recess 51 is thus precisely diametrically opposite the outer contour of that partial section of the projection which points in the direction of the distal end of the syringe body. In the mounted state, the finger flange element 41 surrounds the cylindrical surface of the syringe body 12 in a region that corresponds to an included angle of 180° or more. If the included angle corresponds to more than 180°, a certain elasticity of the finger flange element 41 is favorable, in order to make possible a lateral displacement onto the syringe body 12.

Another contact surface is formed between the other finger flange element 42 and the projection pointing in the direction of opening of the syringe body 12 and/or at least one part of the front side of the syringe body 12, when, after pushing on finger flange element 41, the other finger flange element 42 is closed. A movement in the direction of rotation A can result for closing the two finger flange elements.

In the example, the first mountable finger flange 41 is formed with two elastic spring elements 46 protruding in the direction of the opening of the syringe body, these spring elements engaging in the uptakes 47 of the other finger flange element 42 that are formed precisely diametrically opposite these elements when closed. Both finger flange elements can be securely locked together thereby, whereby a re-opening can be prevented due to the corresponding configuration.

The finger flange 40 further comprises a passage opening, which is formed in the finger flange element 42 as a central, through-opening 44, and which comprises a part of the recess in the finger flange element 41.

The contact surface between finger flange 20, 40, and syringe 10 formed in the mounted state can thus comprise a part of the peripheral surface of the syringe body, in particular at its proximal end 14, and/or a part of the front side of the syringe body 12.

In FIG. 5, a finger flange 40 is schematically illustrated in a top view in an open state suitable for mounting. The illustrated, approximately U-shaped recess 51 is centrally formed for guiding the plunger and runs to the outer edge in two opposite-lying, collar-shaped projecting sections 52. In this embodiment, the plunger or the plunger with a stopper is mounted only after introducing and closing the finger flange 40, in order to be able to push the plunger through the passage opening 44. A backstop function can be created by forming the finger flange of an elastic material in the region of the passage opening 44, so that the passage opening 44 can expand elastically when the plunger or the plunger with a stopper is mounted.

By this form of the recess 51, an engagement of the proximal end of the syringe body can be achieved, which corresponds to an included angle α of more than 180°. In the illustrated example, the included angle α has a size of approximately 220°. In this case, at least the finger flange element 41, particularly in the region of the recess, is elastically formed, so that a lateral displacement onto the syringe body 12 is facilitated. The recess of the finger flange element can also be formed, however, in such a way that an engagement with an included angle of less than 180° is achieved. The finger flange element can be mounted with little expenditure of force thereby.

Figure 6:
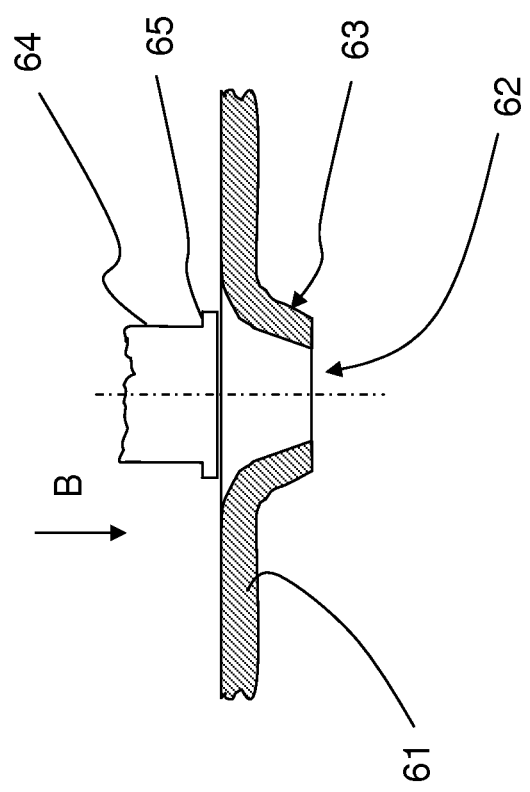
FIG. 6 shows schematically a backstop function.

Finally, a backstop function is shown schematically in FIG. 6. A finger flange element 61 shown in sections and made of an elastic material comprises a passage opening 62. All around the passage opening 62, the finger flange element is formed with a collar-shaped projection 63, which tapers in the direction opposite to the mounting direction of the stopper or of the plunger.

Now, insofar as a stopper 64, which is shown in section, is pushed through the passage opening 62 in mounting direction B, the elastic material of the finger flange element expands, preferably in the region of the collar-shaped projection 63. Due to this expansion of the passage opening 62, the stopper 64 can be pushed through. After the stopper 64 has been pushed through, the expansion of the passage opening 62 is reduced again, and another projection 65 of the stopper 64 prevents a movement in a direction opposite to the mounting direction B. In the same way, a backstop function can also be realized for a plunger (not shown).

The invention also comprises a one-piece finger flange 20, 40, which is designed in order to be able to be connected to a syringe body 12 at its proximal end 14, in particular in the region of the projection 11. The finger flange can comprise two or more finger flange elements 22, 23, 41, 42, which are joined together in movable manner, preferably rotatable. In a preferred embodiment, the finger flange elements are joined together cohesively.

In this case, the cohesive, rotatable connection of the finger flange elements can be provided by a joint or hinge, preferably a film hinge, a foil joint or a film joint.

A finger flange 20, 40 according to the invention can be mounted on a syringe 10. Preferably, in this case, the inner contour of the finger flange is formed precisely diametrically opposite the outer contour of the syringe body 12 on its proximal end 14, in order to create a friction-fit and/or cohesive connection. In the case of a syringe body with a groove on its proximal end, the finger flange accordingly may also have a projection formed precisely diametrically opposite the groove.

In this way, it is possible to retrofit syringes with a finger flange and to equip them with a finger support surface.

On the one hand, the finger flange 20, 40 according to the invention is very easy to mount on the syringe body. In addition, however, it can also be manufactured cost-effectively and in large numbers of pieces, for example, as a one-piece injection molding, or also in a multi-component injection-molding process or in an in-mold process.

In the mounted state, the finger flange is further characterized by protection against disassembling. For this purpose, the locking can be designed so as to obtain an indissoluble lock in closed position of the finger flange elements. In addition, the finger flange can also be fastened resistant to rotation, so that a solid sitting on the syringe is assured. In addition to this, it can also provide tolerance compensation.

LIST OF REFERENCE NUMBERS

| | |
|---|---|
| 10 | Syringe |
| 11 | Projection |
| 12 | Syringe body |
| 13 | Chamber |
| 14 | Proximal end |
| 15 | Distal end |
| 16 | Liquid |
| 17 | Stopper |
| 18 | Plunger |
| 19 | Inner opening |
| 20 | Finger flange |
| 21 | Finger support |
| 22 | Finger flange element |
| 23 | Finger flange element |
| 24 | Locking element |
| 25 | Uptake element |
| 26 | Groove |
| 28 | Center line |
| 33 | Joint or hinge |
| 34 | Recess |
| 35 | Recess |
| 40 | Finger flange |
| 41 | Finger flange element |
| 42 | Finger flange element |
| 43 | Film joint |
| 44 | Passage opening |
| 46 | Spring element |
| 47 | Uptake |
| 48 | Edge |
| 51 | Recess |
| 52 | Section |

-continued

| 61 | Finger flange element (excerpt) |
| 62 | Passage opening |
| 63 | Collar-shaped projection |
| 64 | Stopper |
| 65 | Projection |

What is claimed is:

1. A syringe comprising:
a cylindrical syringe body having a distal end, a proximal end, and a cylindrical chamber for uptake of a liquid substance, the proximal end having an opening and at least one protruding or ring-shaped projection, the at least one projection protruding radially outward over a circumferential surface of the syringe body; and
a finger flange having at least one support surface for a finger, the finger flange being designed in one piece and comprising a first finger flange element and a second finger flange element, the first and second finger flange elements being movably connected to one another between an open position and a closed position,
wherein, when in the closed position, the finger flange is connected in a friction-fit at least partially to the at least one projection and surrounds the at least one projection so that an axial displacement of the finger flange relative to the syringe body is prevented,
wherein the first finger flange element has a recess configured to receive the proximal end of the syringe body into the recess by radial displacement,
wherein the second finger flange element has a central passage opening configured to define a plunger guiding recess,
wherein the first and the second finger flange elements are joined together for movement between the open position and the closed position by rotation about an axis that is perpendicular to a center line of the syringe body,
wherein the first and the second finger flange elements are disposed in offset parallel planes when in the closed position, the offset parallel planes being perpendicular to the center line of the syringe body,
wherein the first and the second finger flange elements, when in the open position, are configured to be positioned on the syringe body without axial displacement,
wherein the first and second finger flange elements, when in the closed position, are locked together to prevent opening, and
wherein the finger flange prevents a plunger and/or a stopper connected to the plunger from being pulled out.

2. The syringe according to claim 1, wherein, when in the closed position, the finger flange is joined in form-fitting manner at least partially with the at least one projection.

3. The syringe according to claim 1, further comprising the stopper in the cylindrical chamber, the stopper being connectable to the plunger through the opening at the proximal end and the plunger guiding recess.

4. The syringe according to claim 3, wherein the finger flange is formed so as to prevent the plunger or the stopper from being pulled out.

5. The syringe according to claim 1, wherein the opening at the proximal end and the plunger guiding recess are configured to receive the plunger with the stopper therethrough.

6. The syringe according to claim 1, wherein the first and the second finger flange elements are joined together by a joint or hinge.

7. The syringe according to claim 6, wherein the joint or hinge comprises a foil or a film.

8. The syringe according to claim 1, wherein the plunger guiding recess has an inner contour that is formed at least partially precisely diametrically opposite an outer contour of the at least one projection.

9. The syringe according to claim 1, wherein the plunger guiding recess has, at least partially, a dimension when compared with the at least one projection sufficient to form the friction-fit.

10. The syringe according to claim 1, wherein the finger flange is formed, at least partially, by a material having sufficient elasticity to compensate for geometric deviations in the syringe body.

11. The syringe according to claim 10, wherein the material comprises is selected from the group consisting of polypropylene (PP), polyethylene (PE), polyoxymethylene (POM), polybutylene terephthalate (PBT), polyamide (PA), polyethersulfone (PES), thermoplastic elastomer (TPE), and glass-fiber-reinforced plastics.

12. The syringe according to claim 1, wherein the first finger flange element surrounds a peripheral surface of the syringe body in a region that corresponds to an included angle of at most 180°.

13. The syringe according to claim 1, wherein the first finger flange element surrounds a peripheral surface of the syringe body in a region that corresponds to an included angle of less than 180°.

14. The syringe according to claim 1, wherein the first finger flange element surrounds a peripheral surface of the syringe body in a region that corresponds to an included angle of less than 175°.

15. The syringe according to claim 1, wherein, when in the closed position, the first and second finger flange elements are latched together and/or are locked indissolubly.

16. The syringe according to claim 1, wherein, when in the closed position, the first and second finger flange elements are locked indissolubly.

17. The syringe according to claim 5, wherein the second finger flange element, at least in a region of the central passage opening, comprises an elastic material so that the central passage opening expands elastically during receipt of the plunger and the stopper therethrough.

18. A finger flange for guiding a plunger that is formed in one piece therethrough, the finger flange comprising:
at least one first and one second finger flange element are joined together in movable manner by rotation to a closed position by rotation about an axis that is perpendicular to but offset from a center line of a syringe body,
wherein the first finger flange element has a recess configured to receive a proximal end of the syringe body into the recess by radial displacement,
wherein the first and the second finger flange elements, when in the open position, are configured to be positioned on the syringe body without axial displacement,
wherein the second finger flange element has a central passage opening configured to define a plunger guiding recess,
wherein the first and second finger flange elements, when in the closed position, are locked together to prevent opening, and
wherein the plunger guiding recess is configured so that, when in the closed position, the plunger and/or a stopper connected to a plunger is prevented from being pulled out.

19. The finger flange according to claim 18, wherein the at least first and second finger flange elements are joined together by a joint or hinge.

20. A finger flange for guiding a plunger received in a syringe body, the finger flange comprising:
   a first finger flange element having a recess configured to receive a proximal end of the syringe body into the recess by radial displacement;
   a second finger flange element having a plunger guiding recess configured to receive a plunger through the plunger guiding recess by axial displacement; and
   a hinge or joint joining the first and second finger flange elements together for movement between an open position and a closed position by rotation about an axis that is perpendicular to but offset from a center line of the syringe body,
   wherein the first and the second finger flange elements, when in the open position, are configured to be positioned on the syringe body without axial displacement,
   wherein the first and second finger flange elements, when in the closed position, are locked together to prevent opening, and
   wherein the plunger guiding recess is configured so that, when in the closed position, the plunger and/or a stopper connected to a plunger is prevented from being pulled out.

21. A syringe comprising:
   a cylindrical syringe body having a distal end, a proximal end, and a cylindrical chamber for uptake of a liquid substance, the proximal end having an opening and at least one protruding ring-shaped or annular projection, the at least one projection protruding radially outward over a circumferential surface of the syringe body; and
   a finger flange having at least one support surface for a finger, the finger flange being designed in one piece and comprising a first finger flange element and a second finger flange element, the first and second finger flange elements being movably connected to one another between an open position and a closed position,
   wherein, when in the closed position, the finger flange is connected in a friction-fit at least partially to the at least one protruding ring-shaped or annular projection and surrounds the at least one projection so that an axial displacement of the finger flange relative to the syringe body is prevented, and
   wherein the first finger flange element has a recess configured to receive the proximal end of the syringe body comprising the projection into the recess in form-fitting manner by radial displacement,
   wherein the second finger flange element has a central passage opening configured to define a plunger guiding recess,
   wherein the first and the second finger flange elements are joined together for movement between the open position and the closed position by rotation about an axis that is perpendicular to a center line of the syringe body,
   wherein the first and second finger flange elements, when in the closed position, are locked together to prevent opening
   wherein the first and the second finger flange elements are disposed in offset parallel planes when in the closed position, the offset parallel planes being perpendicular to the center line of the syringe body, and
   wherein the finger flange prevents a plunger and/or a stopper connected to the plunger from being pulled out.

* * * * *